United States Patent [19]

Singleton et al.

[11] Patent Number: 5,547,657
[45] Date of Patent: Aug. 20, 1996

[54] LOW-IRRITATION ANESTHETIC AND ANTISEPTIC MOUTH RINSE

[75] Inventors: Andy H. Singleton, Kingsport; Crystal L. Kendrick, Church Hill; Reinhold L. Riemer, II, Kingsport; Robin L. Minga, Blountville, all of Tenn.

[73] Assignee: Eastman Chemical Company, Kingsport, Tenn.

[21] Appl. No.: 320,345

[22] Filed: Oct. 11, 1994

[51] Int. Cl.[6] .............................. A61K 7/16; A61K 7/22
[52] U.S. Cl. ................................... 424/49; 424/54
[58] Field of Search ........................... 424/49–58

[56] References Cited

U.S. PATENT DOCUMENTS

| | | |
|---|---|---|
| 4,808,410 | 2/1989 | Kelleher et al. . |
| 4,917,894 | 4/1990 | Bildstein et al. . |
| 4,927,634 | 5/1990 | Kelleher et al. . |
| 5,055,461 | 10/1991 | Kelleher et al. . |
| 5,120,528 | 6/1992 | Chang et al. .............................. 424/49 |
| 5,192,802 | 3/1993 | Rencher . |
| 5,270,031 | 12/1993 | Lim et al. ................................. 424/49 |

FOREIGN PATENT DOCUMENTS

| | | |
|---|---|---|
| 306910 | 3/1989 | European Pat. Off. . |
| 9420087 | 9/1994 | WIPO . |

OTHER PUBLICATIONS

Abstract of Sharma WO/PCT 94/20087A1 (Sep./15/94) CA. 121:238440 (p. 54) Benxocaine DEG 300 DG/G.

Curtis et al EP 306910A1 (Mar./15/89) CA 111:239512 (p. 13–14) (p.40) Benzocaine DEG 600/G.

*Primary Examiner*—Shep K. Rose
*Attorney, Agent, or Firm*—John D. Thallemer

[57] ABSTRACT

The present invention relates to a low-irritation anesthetic and antiseptic mouth rinse. The mouth rinse is freeze-thaw stable and is prepared using polyethylene glycol having a number average molecular weight of 200 to 300 which have been found to be compatible with local anesthetics and other ingredients commonly used in mouth rinses.

12 Claims, No Drawings

5,547,657

LOW-IRRITATION ANESTHETIC AND ANTISEPTIC MOUTH RINSE

FIELD OF THE INVENTION

The present invention relates to a low-irritation anesthetic and antiseptic mouth rinse.

BACKGROUND OF THE INVENTION

Anesthetic mouth rinses on the market typically contain a short chain monohydric alcohol which not only functions as an excellent solvent for the mouth rinse but kills bacteria in the mouth. For example, U.S. Pat. No. 5,270,031 discloses a mouthrinse containing ethyl alcohol and a copolymer of methyl vinyl ether and maleic anhydride. U.S. Pat. No. 5,120,528 disclose a mouthrinse containing ethyl alcohol, glycerine and water. The disadvantages associated with the use of such monohydric alcohols, however, is that they cause burning or stinging effects in the mouth of the user, and may make the mouth more susceptible to cancer. Moreover, the burning or stinging effects are amplified in formulations containing anesthetics which are chemical compounds that induce loss of sensation in the mouth prior to dental procedures. Therefore, it would be advantageous to develop an anesthetic and antiseptic mouth rinse which does not contain monohydric alcohols and eliminates or diminishes the burning sensation that previous formulations exhibit.

The present inventors have unexpectedly determined that an anesthetic and antiseptic mouth rinse may be prepared using polyethylene glycol having a number average molecular weight of 200 to 300 which does not cause a burning sensation in the mouth of the user. The mouth rinse is freeze-thaw stable and is compatible with local anesthetics and other ingredients commonly used in mouth rinses.

SUMMARY OF THE INVENTION

The present invention is directed to a low-irritation anesthetic and antiseptic mouth rinse which is freeze-thaw stable comprising:

(A) 0.1 to 20 weight percent of a topical anesthetic selected from the group consisting of amethocaine, benzocaine, cocaine, and their acid addition salts;

(B) 4 to 87 weight percent of polyethylene glycol having a number average molecular weight of 200 to 300;

(C) 0.01 to 5.0 weight percent of an aromatic organic antiseptic compound having one or more hydroxy groups attached directly to the benzene ring; and (D) 5 to 85 weight percent of a solvent selected from the group consisting of 1,2-propylene glycol, glycerol and combinations thereof, wherein the weight percentages are based on the total mouth rinse formulation.

DESCRIPTION OF THE INVENTION

The anesthetic and antiseptic mouth rinse of the present invention contains a topical anesthetic, polyethylene glycol having a number average molecular weight of 200 to 300, and an aromatic organic compound. The term "nonalcoholic" as used herein shall mean that the mouthrinse of the present invention is free of monohydric alcohols. Preferably, the mouth rinse contains a topical anesthetic, propylene glycol or glycerol, polyethylene glycol having a number average molecular weight of 200 to 300, water, and an aromatic organic compound. More preferably, the mouth rinse contains a topical anesthetic, propylene glycol or glycerol, polyethylene glycol having a number average molecular weight of 200 to 300, an aromatic organic compound, a sweetener, and a flavoring agent.

Component (A) is a topical anesthetic. Preferably, the mouth rinse contains a topical anesthetic, propylene glycol or glycerol, a surfactant, water, an aromatic organic compound, and a flavoring agent. Component (A) is a topical anesthetic. Topical anesthetics are compounds which block nerve conduction when applied topically to nerve tissue in appropriate concentrations. They produce reversible loss of sensation by preventing or diminishing the conduction of sensory nerve impulses near the site of their application or action. Their main site of action is the cell membrane. Local anesthetics could also be described as local analgesics as they are most often used to produce loss of pain without loss of nervous control. A preferred local anesthetic should not be irritating to the tissue to which it is applied, nor should it cause any permanent damage to nerve structure. It should have low systemic toxicity because it is eventually absorbed from its site of application. The time required for the onset of anesthesia should be as short as possible. Furthermore, the action must last long enough to allow time for the contemplated oral surgery or therapy, yet not so long as to entail an extended period of recovery.

Local anesthetics, and their acid addition salts, of the ester type suitable for this invention include: amethocaine (tetracaine, or 2-dimethylaminoethyl 4-butylaminobenzoate); benzocaine (ethyl p-aminobenzoate, or ethyl 4-aminobenzoate); and cocaine (cocainium chloride). Local anesthetics, and their acid addition salts, of the amide type include: Bupivacaine hydrochloride ((±)-(1-butyl-2-piperidyl)formo-2',6' xylidide hydrochloride monohydrate); cinchocaine (dibucaine, or 2-butoxy-N (2-diethylaminoethyl)-quinoline-4 -carboxamide); etidocaine ((±)-2-(N-ethylpropylamino)butyro-2',6'-xylidide hydrochloride); lignocaine (lidocaine); mepivacaine (1-methyl-2-piperidyl)formo-2',6'-xylidide hydrochloride); and prilocaine (propylaminopropiono-o-toluidide hydrochloride). Other local anesthetics, and their acid addition salts, include: Butacaine sulphate (3-dibutylaminopropyl 4-aminobenzoate sulphate; butanilicaine phosphate (2-butylamino-6'-chloroaceto-o-toluidide dihydrogen phosphate); butyl aminobenzoate (butyl 4-aminobenzoate); carticaine hydrochloride (methyl 4-methyl-3-(2-propylaminopropionamido)thiophene2-carboxylate hydrochloride; chloroprocaine hydrochloride (2-diethylaminoethyl 4-amino-2-chlorobenzoate hydrochloride); cyclomethycaine sulphate (3-(2-methylpiperidino)-propyl 4-cyclohexyloxybenzoate hydrogen sulphate); dimethisoquin hydrochloride (2-(3-butyl-1 -isoquinolyloxy)-NN-dimethylethyl-amine hydrochloride); diperodon (3-piperidinopropylene bis(phenylcarbamate) monohydrate); dyclonine hydrochloride (4'-butyoxy-3-piperidinopropiophenone hydrochloride); ethyl chloride (chloroethane); euprocin hydrochloride ((9R) 10,11 -dihydro-6'-(3-methylbutoxy)cinochonan-9-ol dihydrochloride monohydrate); fomocaine (4-[3-(alphaphenoxy-p-tolyl)propyl]morpholine); hexylcaine hydrochloride (2-cyclohexylamino-1-methylethyl benzoate hydrochloride); isobucaine hydrochloride (2-isobutylamino- 2-methylpropyl benzoate hydrochloride); ketocaine hydrochloride (2'-(2-di-isopropylaminoethoxy)butyrophenone hydrochloride); leucinocaine mesylate (2-diethylamino-4-methylpentyl-4-aminobenzoate methanesulphonate); meprylcaine hydrochloride (2-methyl-2-propylaminopropyl benzoate hydrochloride); myrtecaine (2-[2-(10-norpin-2-en-2-yl)ethoxy]triethylamine); octacaine hydrochloride (3-diethylaminobutyranilide hydrochloride); oxybuprocaine hydrochloride (2-diethylaminoethyl 4-amino-3-butoxybenzoate hydrochloride); pramoxine hydrochloride (4-[3-(4-butoxyphenoxy)propyl]morpholine hydrochloride); and proxymetacaine hydrochloride (2-diethylaminoethyl 3-amino-4-propoxybenzoate hydrochloride).

The topical anesthetic, component (A), is present in an amount of 0.1 to 20 weight percent based on the total weight of the mouth rinse formulation. Preferably, the topical anesthetic is benzocaine and is present in an amount of 4 to 15 weight percent, more preferably, 5 to 10 weight percent of the mouth rinse formulation.

Component (B) is polyethylene glycol. The polyethylene glycol has a number average molecular weight of 200 to 300. It is important to note that polyethylene glycol 400 and polyethylene glycol 600 do not provide a stable mouth rinse at temperatures approaching 0° C. The polyethylene glycol is present in an amount of 4 to 87 weight percent of the mouth rinse formulation. Preferably, the polyethylene glycol is present in an amount of 8 to 30 weight percent, more preferable 15 to 20 weight percent of the mouth rinse formulation.

Component (C) is an aromatic organic antiseptic compound having one or more hydroxy groups attached directly to the benzene ring. Examples include phenol, cresol, xylenol, resorcinol, and naphthol, including any isomers of such aromatic organic compounds. The aromatic organic antiseptic compound is added neat or in the form of a solution. The aromatic organic antiseptic compound is present in an amount of 0.01 to 5 weight percent based on the total weight of the mouth rinse formulation. Preferably, the aromatic organic antiseptic compound is phenol and is present in an amount of 0.1 to 1 weight percent, more preferably, 0.4 to 0.8 weight percent of the mouth rinse formulation.

Component (D) is a solvent selected from 1,2-propylene glycol, glycerol or a combination of 1,2-propylene glycol and glycerol. 1,2-Propylene glycol has the formula $CH_3CHOHCH_2OH$. Glycerol has the formula $C_3H_5(OH)_3$. The solvent is present in an amount of 5 to 85 weight percent based on the total weight of the mouth rinse formulation. Preferably, the solvent is propylene glycol and is present in an amount of 50 to 75 weight percent of the mouth rinse formulation. 1,2-Propylene glycol and glycerol dissolve or solubilize the topical anesthetic, component (A), into solution. In addition, 1,2-propylene glycol and glycerol decrease or eliminate the burning and stinging effects that are common with the use of topical anesthetics.

The mouth rinse formulation of the present invention may also contain a surfactant, component (E). Useful surfactants include anionic, nonionic and cationic surfactants provided such surfactants do not deleteriously effect the solubility of the mouth rinse or do not form crystals in the mouthrinse at low temperatures. Specific nonionic surfactants include block copolymers of polyoxyethylene and polyoxypropylene which are available under the tradenames MACOL 27, available from PPG, and PLURACARE 127, available from BASF (CTFA name poloxamer 407). It is important to note that sodium lauryl sulfate which is an anionic surfactant may be used provided the concentration of anesthetic is less than 5 weight percent. Sodium lauryl sulfate used at higher concentrations of anesthetic results in the formation of crystals at low temperatures. Preferably, the surfactant is present in an amount of 1 to 20 weight percent, more preferably, 5 to 10 weight percent of the mouth rinse formulation.

Liquid surfactants may be added neat. However, it may be advantageous to melt the solid surfactants or form an aqueous solution with powder surfactants before addition. It is important to note that greater than 15% water in the mouth rinse formulation causes crystals to form and results in a cloudy formulation. While a cloudy formulation may be acceptable in some instances, a clear mouth rinse is preferred.

The mouth rinse of the present invention may also contain a flavoring agent. Any suitable flavoring agent may be employed. Examples of suitable flavoring agents include flavoring oils such as wintergreen, sassafras, sage, eucalyptus, clove, mint oil, marjoram, cinnamon, grape, cherry, peppermint, lemon and orange, as well as sodium methylsalicylate. Preferably, the total amount of flavoring agent is 0.01 to 10 weight percent, more preferably, 0.1 to 0.5 weight percent of the total mouth rinse formulation.

The mouth rinse of the present invention may also contain a sweetener. Any suitable sweetener may be employed. Suitable sweeteners include sucrose, lactose, maltose, sorbitol, sodium cyclamate, sodium saccharine, aspertame, and other natural or artificial sweeteners. Preferably, the amount of sweetening agent is 0.01 to 10 weight percent, more preferably, 0.1 to 1 weight percent of the total mouth rinse formulation.

The mouth rinse may also contain a fluorine-containing compound which has a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), sodium hexafluorostannate, stannous chlorafluoride sodium fluorozirconate, and sodium monofluorophosphate. These materials, which dissociate or release fluorine-containing ions in water, suitably may be present in an effective but nontoxic amount, usually within the range of about 0.01 to 1 percent by weight of the water soluble fluorine content thereof.

Various other additives may be incorporated in the anesthetic mouth of this invention. Examples thereof are antibacterial agents, coloring or whitening agents, preservatives, chlorophyll compounds, ammoniated materials such as urea, diammoniumphosphate and mixtures thereof, and other constituents. These adjuvants are incorporated in the instant compositions in amounts which do not substantially adversely effect the properties and characteristics suitably selected and used in proper amount depending upon the particular type of preparation involved.

The anesthetic and antiseptic mouth rinse of the present invention may be prepared at room temperature (23° C.) or using low heat (<90° C.) by mixing the topical anesthetic, component (A), polyethylene glycol, component (B), and optionally a solvent, component (D), until a solution is obtained. Optionally, a surfactant, component (E), is added to the solution and mixing is continued. Optional ingredients such as vitamin E and a sweetener are also added and mixed in the solution. The aromatic organic antiseptic compound, component (C), is added and mixed until a solution is obtained. A flavoring agent is optionally mixed into the solution. A clear mouth rinse is obtained.

The mouth rinse of the present invention may be used anywhere where relief from tooth or gum pain is desired. The anesthetic mouth rinse is especially useful in dental offices as a pre-examination/dental work mouth rinse. The anesthetic mouth rinse causes a numbing sensation to the oral tissues, so that the dental patient feels less discomfort during the dental examination and minor dental work, such as probing of cavity areas and/or existing fillings, injecting novocaine or other such similar anesthetics, irrigating the oral cavity with water and/or compressed air for drying of the oral tissues, scraping and cleaning teeth.

The process of the present invention will be further illustrated by a consideration of the following examples, which are intended to be exemplary of the invention.

EXAMPLE I

A mouth rinse having the following formula was prepared.

| Formulation | weight % |
| --- | --- |
| Propylene glycol | 70.0 |
| Benzocaine | 7.5 |
| Polyethylene glycol 200 | 17.0 |
| Vitamin E 5-87 | 0.1 |
| Sodium saccharin solution (11%) | 4.6 |
| Phenol | 0.6 |
| Cherry Flavor | 0.2 |

The mouth rinse was prepared by mixing the benzocaine and propylene glycol at a temperature of 30°–40° C. A temperature of 30°–40° C. was maintained and polyethylene glycol 200 was added and mixed until dispersed. Vitamin E was added and mixed until dispersed. The heat was turned off and a sodium saccharin solution in water was added. Mixing was continued while the solution cooled to 25° C. Phenol was added with mixing. Flavoring was added with mixing.

Irritation, taste, and numbing sensation of the mouth rinse was determined by having twenty people sample each mouth rinse and report on the level of irritation, taste and numbing effect. Irritation was reported as none, low, or high. Taste was reported as pleasant or unpleasant. The numbing effect was measured in minutes. Irritation was reported as: 100% none. Taste was reported as: 100% pleasant. Numbing effect lasted for 15 to 20 minutes.

The sample was placed in a refrigerator at a temperature of −20° C. for 30 days. No crystal growth was observed.

EXAMPLE II

A mouth rinse having the following formula was prepared.

| Formulation | weight % |
| --- | --- |
| Propylene glycol | 70.0 |
| Benzocaine | 7.5 |
| Polyethylene glycol 200 | 1.0 |
| Vitamin E 5-87 | 0.1 |
| Sodium lauryl sulfate (30%) | 15.0 |
| Sodium Saccharin solution (11%) | 5.6 |
| Phenol | 0.6 |
| Cherry Flavor | 0.2 |

The mouth rinse was prepared by mixing the benzocaine and propylene glycol at a temperature of 30°–40° C. A temperature of 30°–40° C. was maintained and polyethylene glycol 200 was added and mixed until dispersed. Sodium lauryl sulfate was added and mixed until dispersed. Vitamin E was added and mixed until dispersed. The heat was turned off and a sodium saccharin solution in water was added. Mixing was continued while the solution cooled to 25C. Phenol was added with mixing. Flavoring was added with mixing.

Irritation was reported as: 70% high, 30% low. Taste was reported as: 90% unpleasant, 10% pleasant. Numbing effect lasted for 15 to 20 minutes.

The sample was placed in a refrigerator at a temperature of 8° C. Crystal growth was observed within 24 hours.

EXAMPLE III

A mouth rinse having the following formula was prepared using the procedure as set forth in Example II.

| Formulation | weight % |
| --- | --- |
| Propylene glycol | 70.5 |
| Benzocaine | 7.5 |
| Polyethylene glycol 200 | 1.5 |
| Sodium lauryl sulfate (30%) | 15.0 |
| Vitamin E 5-87 | 0.1 |
| Sodium Saccharin solution (11%) | 4.6 |
| Phenol | 0.6 |
| Cherry Flavor | 0.2 |

Irritation was reported as: 70% high, 30% low. Taste was reported as: 90% unpleasant, 10% pleasant. Numbing effect lasted for 15 to 20 minutes.

The sample was placed in a refrigerator at a temperature of 8° C. Crystal growth was observed within 24 hours.

EXAMPLE IV

A mouth rinse having the following formula was prepared using the procedure as set forth in Example II.

| Formulation | weight % |
| --- | --- |
| Propylene glycol | 70.0 |
| Benzocaine | 7.5 |
| Polyethylene glycol 200 | 2.0 |
| Sodium lauryl sulfate (30%) | 15.0 |
| Vitamin E 5-87 | 0.1 |
| Sodium Saccharin solution (11%) | 4.6 |
| Phenol | 0.6 |
| Cherry Flavor | 0.2 |

Irritation was reported as: 70% high, 30% low. Taste was reported as: 90% unpleasant, 10% pleasant. Numbing effect lasted for 15 to 20 minutes.

The sample was placed in a refrigerator at a temperature of 8° C. Crystal growth was observed within hours.

EXAMPLE V

A mouth rinse having the following formula was prepared.

| Formulation | weight % |
| --- | --- |
| Benzocaine | 7.5 |
| Polyethylene glycol 200 | 71.0 |
| Sodium lauryl sulfate (30%) | 15.0 |
| Vitamin E 5-87 | 0.1 |
| Sodium Saccharin solution (11%) | 5.6 |
| Phenol | 0.6 |
| Grape Flavor | 0.2 |

The mouth rinse was prepared by mixing the benzocaine and polyethylene glycol 200 at a temperature of 30° C. A temperature of 30° C. was maintained and sodium lauryl sulfate was added and mixed until dispersed. Vitamin E was added and mixed until dispersed. The heat was turned off and a sodium saccharin solution in water was added. Mixing was continued while the solution cooled to 25° C. Phenol was added with mixing. Flavoring was added with mixing.

Irritation was reported as: 70% high, 30% low. Taste was reported as: 80% unpleasant, 20% pleasant. Numbing effect lasted for 15 to 20 minutes.

The sample was placed in a refrigerator at a temperature of 8° C. for 7 days. No crystal growth was observed.

EXAMPLE VI

A mouth rinse having the following formula was prepared using the procedure as set forth in Example II.

| Formulation | weight % |
|---|---|
| Propylene glycol | 70.0 |
| Benzocaine | 7.5 |
| Polyethylene glycol 400 | 2.0 |
| Sodium lauryl sulfate (30%) | 15.0 |
| Vitamin E 5-87 | 0.1 |
| Sodium Saccharin solution (11%) | 4.6 |
| Phenol | 0.6 |
| Cherry Flavor | 0.2 |

The sample appeared cloudy. The sample was placed in a refrigerator at a temperature of 8° C. Crystal growth was observed within 24 hours.

EXAMPLE VII

A mouth rinse having the following formula was prepared using the procedure as set forth in Example II.

| Formulation | weight % |
|---|---|
| Propylene glycol | 70.0 |
| Benzocaine | 7.5 |
| Polyethylene glycol 600 | 2.0 |
| Sodium lauryl sulfate (30%) | 15.0 |
| Vitamin E 5-87 | 0.1 |
| Sodium Saccharin solution (11%) | 4.6 |
| Phenol | 0.6 |
| Cherry Flavor | 0.2 |

The sample appeared cloudy. The sample was placed in a refrigerator at a temperature of 8° C. Crystal growth was observed within 24 hours.

EXAMPLE VIII

A mouth rinse having the following formula was prepared using the procedure as set forth in Example II.

| Formulation | weight % |
|---|---|
| Propylene glycol | 70.5 |
| Benzocaine | 7.5 |
| Polyethylene glycol 200 | 0.5 |
| Vitamin E 5-87 | 0.1 |
| Sodium lauryl sulfate (30%) | 15.0 |
| Sodium saccharin solution (11%) | 5.6 |
| Phenol | 0.6 |
| Grape Flavor | 0.2 |

The sample was placed in a refrigerator at a temperature of 8° C. Large needle-like crystals were observed were observed within 24 hours.

EXAMPLE IX

A mouth rinse having the following formula was prepared using the procedure as set forth in Example I.

| Formulation | weight % |
|---|---|
| Propylene glycol | 77.0 |
| Benzocaine | 7.5 |
| Polyethylene glycol 200 | 10.0 |
| Vitamin E 5-87 | 0.1 |
| Sodium Saccharin solution (11%) | 4.6 |
| Phenol | 0.6 |
| Cherry Flavor | 0.2 |

Irritation was reported as: 90% none, 10% low. Taste was reported as: 95% pleasant, 5% unpleasant. Numbing effect lasted for 15 to 20 minutes.

The sample was placed in a refrigerator at a temperature of 8° C. for 30 days. No crystal growth was observed.

EXAMPLE X

A mouth rinse having the following formula was prepared using the procedure as set forth in Example I.

| Formulation | weight % |
|---|---|
| Propylene glycol | 72.0 |
| Benzocaine | 7.5 |
| Polyethylene glycol 200 | 15.0 |
| Vitamin E 5-87 | 0.1 |
| Sodium Saccharin solution (11%) | 4.6 |
| Phenol | 0.6 |
| Cherry Flavor | 0.2 |

Irritation was reported as: 100% none. Taste was reported as: 100% pleasant. Numbing effect lasted for 15 to 20 minutes.

The sample was placed in a refrigerator at a temperature of 8° C. for 30 days. No crystal growth was observed.

EXAMPLE XI

A mouth rinse having the following formula was prepared using the procedure as set forth in Example I.

| Formulation | weight % |
|---|---|
| Propylene glycol | 67.0 |
| Benzocaine | 7.5 |
| Polyethylene glycol 200 | 20.0 |
| Vitamin E 5-87 | 0.1 |
| Sodium Saccharin solution (11%) | 4.6 |
| Phenol | 0.6 |
| Cherry Flavor | 0.2 |

Irritation was reported as: 90% none, 10% low. Taste was reported as: 95% pleasant, 5% unpleasant. Numbing effect lasted for 15 to 20 minutes.

The sample was placed in a refrigerator at a temperature of 8° C. for 30 days. No crystal growth was observed.

EXAMPLE XII

A mouth rinse having the following formula was prepared using the procedure as set forth in Example I.

| Formulation | weight % |
|---|---|
| Propylene glycol | 57.0 |
| Benzocaine | 7.5 |
| Polyethylene glycol 200 | 30.0 |
| Vitamin E 5-87 | 0.1 |
| Sodium saccharin solution (11%) | 4.6 |
| Phenol | 0.6 |

-continued

| Formulation | weight % |
| --- | --- |
| Cherry Flavor | 0.2 |

The sample was placed in a refrigerator at a temperature of 8° C. for 30 days. No crystal growth was observed.

EXAMPLE XIII

A mouth rinse having the following formula was prepared.

| Formulation | weight % |
| --- | --- |
| Propylene glycol | 70.0 |
| Benzocaine | 7.5 |
| POLOXAMER 407 | 2.0 |
| Sodium Lauryl Sulfate (30%) | 15.0 |
| Vitamin E 5-87 | 0.1 |
| Sodium Saccharin solution (11%) | 4.6 |
| Phenol | 0.6 |
| Cherry Flavor | 0.2 |

The mouth rinse was prepared by mixing the benzocaine and propylene glycol at a temperature of 35°–40° C. The temperature was maintained and POLOXAMER 407 was added and mixed until dispersed. Sodium lauryl sulfate was added and mixed until dispersed. The temperature was reduced to 30°–35° C. and vitamin E was added and mixed until dispersed. The heat was turned off and a sodium saccharin solution in water was added. Mixing was continued while the solution cooled to 25° C. Phenol was added with mixing. Flavoring was added with mixing.

Irritation was reported as: 70% high, 30% low. Taste was reported as: 100% unpleasant. Numbing effect lasted for 15 to 20 minutes. The mouth rinse was refrigerated at 8° C., and crystals formed after 3 hours.

EXAMPLE XIV

A mouth rinse having the same formula as in Example XIII was prepared by the following procedure at room temperature.

The mouth rinse was prepared by mixing the benzocaine and propylene glycol at a temperature of 23° C. POLOXAMER 407 was added and mixed until dispersed. Sodium lauryl sulfate was added and mixed until dispersed. Vitamin E was added and mixed until dispersed. A sodium saccharin solution in water was added. Mixing was continued and phenol was added. Flavoring was added with mixing. The mouth rinse was refrigerated at 8° C., and crystals formed after 3 hours.

EXAMPLE XV

A mouth rinse having the same formula as in Example XIII was prepared except that the amount of POLOXAMER 407 was increased from 2 weight percent to 7 weight percent and the amount of sodium lauryl sulfate solution was decreased from 15 weight percent to 10 weight percent.

Irritation was reported as: 50% high, 50% low. Taste was reported as: 100% unpleasant. Numbing effect lasted for 15 to 20 minutes. The mouth rinse was refrigerated at 8° C., and crystals formed after 3 hours.

EXAMPLE XVI

A mouth rinse having the same formula as in Example I was prepared by the following procedure at room temperature.

The mouth rinse was prepared by mixing the benzocaine and propylene glycol at room temperature, about 23° C. Polyethylene glycol 200 was added and mixed until dispersed. Vitamin E was added and mixed until dispersed. A sodium saccharin solution in water was added. Mixing was continued until the sodium saccharin dispersed. Phenol was added with mixing. Flavoring was added with mixing.

Irritation was reported as: 100% none. Taste was reported as: 100% pleasant. Numbing effect lasted for 15 to 20 minutes. The sample was placed in a refrigerator at a temperature of −20° C. for 30 days. No crystal growth was observed.

EXAMPLE XVII

A mouth rinse having the same formula as in Example II was prepared by the following procedure at room temperature.

The mouth rinse was prepared by mixing the benzocaine and propylene glycol at a temperature of about 23° C. Room temperature was maintained and polyethylene glycol 200 was added and mixed until dispersed. Sodium lauryl sulfate was added and mixed until dispersed. Vitamin E was added and mixed until dispersed. A sodium saccharin solution in water was added. Mixing was continued and phenol was added. Flavoring was added with mixing.

Irritation was reported as: 70% high, 30% low. Taste was reported as: 90% unpleasant, 10% pleasant. Numbing effect lasted for 15 to 20 minutes.

The sample was placed in a refrigerator at a temperature of 8° C. Crystal growth was observed within 24 hours.

EXAMPLE XVIII

A mouth rinse having the following formula was prepared.

| Formulation | weight % |
| --- | --- |
| Propylene glycol | 70.0 |
| Benzocaine | 7.5 |
| POLOXAMER 407 | 17.0 |
| Vitamin E 5-87 | 0.1 |
| Sodium Saccharin solution (11%) | 4.6 |
| Phenol | 0.6 |
| Cherry Flavor | 0.2 |

The mouth rinse was prepared by mixing the benzocaine and propylene glycol 200 at a temperature of 50° C. A temperature of 50° C. was maintained and POLOXAMER 407 was added and mixed until dispersed. Vitamin E was added and mixed until dispersed. The heat was turned off and a sodium saccharin solution in water was added. Mixing was continued while the solution cooled to 25° C. Phenol was added with mixing. Flavoring was added with mixing.

The sample was placed in a refrigerator at a temperature of −20° C. After 1 hour the sample turned cloudy. After 72 hours, the sample was removed from the refrigerator and allowed to thaw to room temperature. Upon reaching room temperature, the sample remained cloudy.

EXAMPLE XIX

A mouth rinse having the following formula was prepared.

| Formulation | weight |
| --- | --- |
| Propylene glycol | 70.0 |
| Benzocaine | 7.5 |
| Polyethylene glycol 200 | 8.5 |
| POLOXAMER 407 | 8.5 |

-continued

| Formulation | weight |
|---|---|
| Vitamin E 5-87 | 0.1 |
| Sodium Saccharin solution (11%) | 4.6 |
| Phenol | 0.6 |
| Cherry Flavor | 0.2 |

The mouth rinse was prepared according to the procedure set forth in Example XVIII, except that 8.5 weight percent of polyethylene glycol and 8.5 weight percent POLOXAMER 407 was used as the surfactant.

The sample was placed in a refrigerator at a temperature of −20° C. for 3 days. No crystal growth was observed. After 72 hours, the sample was removed from the refrigerator and allowed to warm to room temperature. Upon reaching room temperature, the sample was clear and no crystals were observed.

EXAMPLE XX

A mouth rinse having the following formula was prepared.

| Formulation | weight % |
|---|---|
| Propylene glycol | 17.0 |
| Benzocaine | 7.5 |
| Polyethylene glycol 200 | 70.0 |
| Vitamin E 5-87 | 0.1 |
| Sodium Saccharin solution (11%) | 4.6 |
| Phenol | 0.6 |
| Cherry Flavor | 0.2 |

The mouth rinse was prepared according to the procedure set forth in Example I, except that the amounts of polyethylene glycol and propylene glycol were interchanged.

The sample was placed in a refrigerator at a temperature of 8° C. for 3 days. No crystal growth was observed. After 72 hours, the sample was removed from the refrigerator and allowed to warm to room temperature. Upon reaching room temperature, the sample was clear and no crystals were observed.

EXAMPLE XXI

A mouth rinse having the following formula was prepared.

| Formulation | weight % |
|---|---|
| Propylene glycol | 7.0 |
| Benzocaine | 7.5 |
| Polyethylene glycol 200 | 80.0 |
| Vitamin E 5-87 | 0.1 |
| Sodium Saccharin solution (11%) | 4.6 |
| Phenol | 0.6 |
| Cherry Flavor | 0.2 |

The mouth rinse was prepared according to the procedure set forth in Example I, except that the amounts of polyethylene glycol and propylene glycol were changed.

The sample was placed in a refrigerator at a temperature of 8° C. for 3 days. No crystal growth was observed. After 72 hours, the sample was removed from the refrigerator and allowed to warm to room temperature. Upon reaching room temperature, the sample was clear and no crystals were observed.

EXAMPLE XXII

A mouth rinse having the following formula was prepared.

| Formulation | weight % |
|---|---|
| Propylene glycol | 87.0 |
| Benzocaine | 7.5 |
| Vitamin E 5-87 | 0.1 |
| Sodium Saccharin solution (11%) | 4.6 |
| Phenol | 0.6 |
| Cherry Flavor | 0.2 |

The mouth rinse was prepared according to the procedure set forth in Example I, except that a greater amount of propylene glycol was used and no polyethylene glycol was added.

The sample was placed in a refrigerator at a temperature of 8° C. Within 12 hours crystals formed.

The anesthetic and antiseptic mouth rinse of the present invention does not cause irritation of the gums of the mouth. The mouth rinse is freeze-thaw stable and is prepared using polyethylene glycol having a number average molecular weight of 200 to 300 which has been found to be compatible with anesthetic compounds, antiseptic compounds, sweeteners, flavoring agents and other ingredients used in mouth rinses.

Many variations will suggest themselves to those skilled in this art in light of the above detailed description. All such obvious modifications are within the full intended scope of the appended claims.

What is claimed is:

1. A nonalcoholic low-irritation anesthetic and antiseptic mouth rinse which is stable consisting essentially of:
    (A) 0.1 to 20 weight percent of a topical anesthetic selected from the group consisting of amethocaine, benzocaine, cocaine, and their acid addition salts;
    (B) 4 to 87 weight percent of polyethylene glycol having a number average molecular weight of 200 to 300; and
    (C) 0.01 to 5.0 weight percent of an aromatic organic antiseptic compound having one or more hydroxy groups attached directly to the benzene ring,
wherein the weight percentages are based on the total mouth rinse formulation.

2. A nonalcoholic low-irritation anesthetic and antiseptic mouth rinse which is stable consisting essentially of:
    (A) 0.1 to 20 weight percent of a topical anesthetic selected from the group consisting of amethocaine, benzocaine, cocaine, and their acid addition salts;
    (B) 4 to 87 weight percent of polyethylene glycol having a number average molecular weight of 200 to 300;
    (C) 0.01 to 5.0 weight percent of an aromatic organic antiseptic compound having one or more hydroxy groups attached directly to the benzene ring; and
    (D) 5 to 85 weight percent of a solvent selected from the group consisting of 1,2-propylene glycol, glycerol and combinations thereof,
wherein the weight percentages are based on the total mouth rinse formulation.

3. A nonalcoholic low-irritation anesthetic and antiseptic mouth rinse which is stable consisting essentially of:
    (A) 5 to 10 weight percent of a topical anesthetic selected from the group consisting of amethocaine, benzocaine, and cocaine;
    (B) 15 to 20 weight percent of polyethylene glycol having a number average molecular weight of 200 to 300;

(C) 0.4 to 0.8 weight percent of an aromatic organic antiseptic compound having one or more hydroxy groups attached directly to the benzene ring, (D) 50 to 75 weight percent of a solvent selected from the group consisting of 1,2-propylene glycol, glycerol and combinations thereof; and (E) 1 to 20 weight percent of a surfactant, wherein the weight percentages are based on the total mouth rinse formulation.

4. The mouth rinse according to claim 1 wherein the topical anesthetic, component (A), is benzocaine.

5. The mouth rinse according to claim 1 wherein the antiseptic, component (C), is phenol.

6. The mouth rinse according to claim 3 wherein the surfactant, component (E), is present in an amount of 5 to 10 weight percent.

7. The mouth rinse according to claim 1 which additionally contains 0.01 to 10.0 weight percent a flavoring agent.

8. The mouth rinse according to claim 7 wherein the flavoring agent is present in an amount of 0.1 to 0.5 weight percent.

9. The mouth rinse according to claim 1 which additionally contains 0.01 to 10 weight percent of a sweetener.

10. The mouth rinse according to claim 9 wherein the sweetener is present in an amount of 0.1 to 1 weight percent.

11. The formulation of claim 3 wherein the surfactant, component (E), is a block copolymer of polyoxyethylene and polyoxypropylene.

12. A process which does not involve heating for preparing a nonalcoholic low-irritation anesthetic and antiseptic mouth rinse which is stable comprising the steps of:

(I) mixing 0.1 to 20 weight percent of a topical anesthetic selected from the group consisting of amethocaine, benzocaine, cocaine, and their acid addition salts, and 5 to 85 weight percent of a solvent selected from the group consisting of 1,2-propylene glycol, glycerol and combinations thereof, to form a clear solution;

(II) adding 4 to 85 weight percent of polyethylene glycol having a number average molecular weight of 200 to 300 to the clear solution of Step (I) and agitating until the solution turns clear;

(III) adding 0.1 to 10 weight percent of a sweetener and 0.01 to 5.0 weight percent of an aromatic organic antiseptic compound having one or more hydroxy groups attached directly to the benzene ring to the clear solution of Step (II) and agitating until the solution turns clear; and (IV) adding with agitation 0.01 to 10 weight percent of a flavoring agent to form a clear mouth rinse, wherein the weight percentages are based on the total mouth rinse formulation.

* * * * *